(12) United States Patent
Nakahara et al.

(10) Patent No.: US 10,609,943 B2
(45) Date of Patent: Apr. 7, 2020

(54) KOJI STARTER FOR FERMENTATION, KOJI FOR FERMENTATION, AND SEASONING

(71) Applicant: KIKKOMAN CORPORATION, Noda-shi, Chiba (JP)

(72) Inventors: Takeharu Nakahara, Noda (JP); Yohei Shinozaki, Noda (JP); Kazuki Shiga, Noda (JP); Tatsuya Yamazaki, Noda (JP)

(73) Assignee: KIKKOMAN CORPORATION, Noda-shi, Chiba (JP)

( * ) Notice: Subject to any disclaimer, the term of this patent is extended or adjusted under 35 U.S.C. 154(b) by 0 days.

(21) Appl. No.: 15/312,463

(22) PCT Filed: May 20, 2015

(86) PCT No.: PCT/JP2015/064389
§ 371 (c)(1),
(2) Date: Nov. 18, 2016

(87) PCT Pub. No.: WO2015/178399
PCT Pub. Date: Nov. 26, 2015

(65) Prior Publication Data
US 2017/0119035 A1 May 4, 2017

(30) Foreign Application Priority Data
May 21, 2014 (JP) .................... 2014-105709

(51) Int. Cl.
| C12N 1/14 | (2006.01) |
| A23L 27/50 | (2016.01) |
| A23L 27/10 | (2016.01) |
| A23L 27/24 | (2016.01) |

(52) U.S. Cl.
CPC ............ *A23L 27/50* (2016.08); *A23L 27/10* (2016.08); *A23L 27/24* (2016.08); *C12N 1/14* (2013.01); *A23V 2002/00* (2013.01)

(58) Field of Classification Search
CPC .......... A23L 27/50; A23L 27/10; A23L 27/24; C12N 1/14

USPC .......................................................... 426/44
See application file for complete search history.

(56) References Cited

U.S. PATENT DOCUMENTS

2009/0258110 A1  10/2009 Sato

FOREIGN PATENT DOCUMENTS

| JP | 53-056393 A | 5/1978 |
| JP | 2009-171959 A | 8/2009 |
| JP | 2014-110771 | * 6/2014 ............ A23L 1/221 |
| JP | 2014-110771 A | 6/2014 |
| JP | 5702014 B1 | 4/2015 |
| WO | 2007/058061 A1 | 5/2007 |

OTHER PUBLICATIONS

JP-2014-110-771-Machine Translation. (Year: 2014).*
Xin, F. et al. 2010. Applied Biochem Biotechnol. 162: 295-306 (Year: 2010).*
Muangthai, P. et al. Sci. Tech. J. 2007. 7: 106-112 (Year: 2007).*
International Search Report of PCT/JP2015/064389 dated Aug. 11, 2015 [PCT/ISA/210] English Translation.
Nakahara, T. et al., "Antihypertensive Effect of Peptide-Enriched Soy Sauce-Like Seasoning and Identification of Its Angiotensin I-Converting Enzyme Inhibitory Substances", Journal of Agricultural and Food Chemistry Article, 2010, vol. 58, pp. 821-827.
Nakahara, T., et al., "Antihypertensive Mechanism of a Peptide-Enriched Soy Sauce-Like Seasoning: The Active Constituents and Its Suppressive Effect on Renin-Angiotensin-Aldosterone System", Journal of Food Science, vol. 76, No. 8, 2011, pp. H201-H206.
Jin, F.X.-, et al., "Miso and Soy sauce like Seasoning Research and Their Research System of China", Jorunal of the Brewing Society of Japan, 1994, vol. 89, Issue 9, pp. 691-697 (8 pages).

* cited by examiner

*Primary Examiner* — Hamid R Badr
(74) *Attorney, Agent, or Firm* — Sughrue Mion, PLLC

(57) ABSTRACT

A seed koji (*Aspergillus* starter) for brewing is provided. The seed koji is obtained by inoculating koji mold(s) belonging to an *Aspergillus* genus into a seed koji raw material, where the seed koji raw material is a pea.

9 Claims, No Drawings

KOJI STARTER FOR FERMENTATION, KOJI FOR FERMENTATION, AND SEASONING

CROSS REFERENCE TO RELATED APPLICATIONS

This application is a National Stage of International Application No. PCT/JP2015/064389, filed May 20, 2015, claiming priority based on Japanese Patent Application No. 2014-105709, filed May 21, 2014, the contents of all of which are incorporated herein by reference in their entirety.

TECHNICAL FIELD

The present invention relates to seed koji (*Aspergillus* starter) for brewing, koji (*Aspergillus* culture with cereals) for brewing, and soy sauce-like seasoning obtained without the use of any food item containing an allergenic substance as raw material.

BACKGROUND ART

In the recent years, health hazards (hereinafter, called food allergies) arising from food items containing an allergenic substance (hereinafter, called an allergen) have been seen here and there across the whole world. Food allergies occur when the body's immune system reacts with a particular type of substance or component contained in a food item. Since currently there is no definitive treatment method, the most assuring way of preventing food allergies is avoiding the intake of the food items containing the allergens. An allergic symptom has a possibility to even threaten one's life, and thus, the labeling of allergen-containing raw materials included in food items is imperative for an allergy patient.

Against such a background, a 1999 Session of a Joint FAO/WHO Food Standards Programme (Codex Alimentarius Commission) agreed that labeling of foods containing eight kinds of raw materials known as allergens must indicate that the food contains such substances, and the member nations are now required to consolidate the specific labeling method suitable for their respective legal systems.

In Japan, it was stipulated by the then Ministry of Health, Labor and Welfare that in view of the extent and frequency of the past health problems, etc., if 25 specific raw materials proven to induce severe allergy symptoms were included, the raw materials must be indicated (currently the Consumer Affairs Agency has the jurisdiction, and a total of 27 items including 7 items for which labeling is mandatory and 20 items for which labeling is recommended are included).

Soy sauce, which is a traditional fermented seasoning of Japan and is indispensable in Japan's dietary culture, is obtained by fermenting and brewing koji, which is prepared from soybean and wheat, and a salt solution. However, both soybean and wheat have been listed as food items containing allergens within Japan and in CODEX.

Although it is believed that the allergens are reduced in soy sauce since the raw materials are broken down by the enzymes in koji, patients allergic to soybean or wheat were not possible to use soy sauce depending on the extent of health hazards. Particularly, cereals containing gluten, such as wheat, are known to cause severe symptoms in patients with celiac disease, and the development of gluten-free food items is in demand across the world. Thus, there is a strong demand for substitute seasonings having the taste and aroma of soy sauce, without the use of any food items containing allergens (hereinafter, called allergen-free).

In response to such a demand, there have been disclosed methods that do not use soybean and wheat, such as a method of producing koji using horse bean, and then performing fermentation and maturation by adding salt water (for example, see Patent Document 1), a method of producing koji using a mixture of mustard seeds and corn, and then performing fermentation and maturation by adding salt water (for example, see Patent Document 2), a method of producing a soy sauce-like liquid seasoning with millet as the main constituent (for example, see Patent Document 3), a method of producing a fermented seasoning with *Perilla ocymoides* as the raw material (for example, see Patent Document 4), a method of producing fish sauce (for example, see Patent Document 5), and a method of producing soy sauce-like seasoning with tomato as the raw material (for example, see Patent Document 6). Although horse bean is not considered as a food item containing an allergen, the fact that horse bean causes favism is seen as a problem in all parts of the Mediterranean coast, North Africa, and central Asia (for example, see Patent Document 1). Moreover, since it has the distinctive flavor of horse bean even after being formed into a soy sauce-like seasoning, it may be difficult to use it as a substitute of soy sauce for certain purposes. In the method using a mixture of mustard seeds and corn, the flavor derived from mustard seeds, which are the raw material for spice, is still retained, and umami and aroma is also insufficient. As for the liquid seasoning with millet as the main constituent, and fermented liquid seasoning with *Perilla ocymoides* as the raw material, it is not only difficult to acquire the respective raw materials in a cheap and stable manner, but also difficult to use such items as substitute seasonings of soy sauce due to their distinctive flavor. While fish sauce does not use soybean and wheat, its flavor is significantly different from the regular soy sauce, and it is difficult to use it as a substitute seasoning. Further, some varieties of fish themselves are considered to be food items containing allergens, and therefore, they were inappropriate as allergen-free soy sauce-like seasonings.

The field pea plant (*Pisum sativum* L.) has been widely cultivated since past, and peas that are the seeds of the field pea plant are widely eaten around the world as roasted or boiled beans, uguisu-an (sweet green bean jam), ingredients of salads and stews, raw material of snack bars, and the like. Therefore, it is possible to acquire peas in a cheap and stable manner as raw material of food items. Peas are not indicated as specific raw materials containing the above-mentioned allergens specified within Japan and CODEX, and food items using peas as a raw material are possible to be consumed safely even by patients allergic to soybean and wheat.

As a technique of using peas as the raw material of fermented seasoning, a method of producing soy sauce in which field peas are used as the filled raw material is known (Patent Document 7). However, the purpose of the invention is lightening of the soy sauce, and not the realization of allergen-free, and therefore, it only uses field peas (peas) instead of the regular filled raw material of soybean and wheat, and does not comment on the raw material used in the production of seed koji.

Seed koji is a starter microorganism that is added to the koji-making raw material as a supply source of koji mold in the koji-making process for soy sauce, fermented soybean paste, sake, mirin (sweet sake for cooking), etc., and generally, the koji mold is cultured on the seed koji raw material, such as wheat bran and rice, and spores are produced. From the past, the seed koji have been widely used, and the technique of adding seed koji during koji-making is indispensable for the brewing industry even today.

Allergy symptoms may appear even from a minute amount of allergen, and in some circumstances, a severe allergy symptom such as anaphylactic shock may be induced, which may be life-threatening. Therefore, in order to produce allergen-free soy sauce, it is necessary to avoid the carryover of allergens that are derived not only from the main raw material, but also from the auxiliary raw materials such as the seed koji raw material used in the production of seed koji.

Wheat bran is used in the preparation of koji mold starter (seed koji) used in koji-making of general soy sauce koji. However, wheat bran is a part of the skin of wheat that is produced during the milling process for wheat flour, and includes mixtures such as the seed coat, perisperm, and embryo of wheat seeds. Therefore, from the viewpoint of carryover of allergens derived from wheat, it is not possible to use wheat bran in allergen-free soy sauce, which was a problem.

Soy sauce that does not use wheat as a raw material is provided to patients allergic to wheat. For example, brewed food items, such as soy sauce that makes use of seed koji using only raw materials derived from soybean and that does not at all contain components derived from wheat, are known (Patent Document 8). However, soybean is listed as one of the 20 allergens recommended to be labeled on the basis of the Food Sanitation Act, and of the item to be labeled according to CODEX specified by the Joint FAO/WHO Food Standards Programme (Codex Alimentarius Commission), and still it is not possible to realize the purpose of obtaining allergen-free soy sauce.

PRIOR ART DOCUMENT

Patent Document

Patent Document 1: Japanese Unexamined Patent Application Publication No. 2006-122002
Patent Document 2: Japanese Unexamined Patent Application Publication No. 2008-237183
Patent Document 3: Japanese Unexamined Patent Application Publication No. H8-196232
Patent Document 4: Japanese Unexamined Patent Application Publication No. 2009-171959
Patent Document 5: Japanese Unexamined Patent Application Publication No. 2005-261349
Patent Document 6: Japanese Unexamined Patent Application Publication No. 2012-187096
Patent Document 7: Japanese Unexamined Patent Application Publication No. S53-56393
Patent Document 8: Publication of Japanese Patent No. 4908424

Non Patent Document

Non Patent Document 1 "Food allergy: adverse reactions to food and food additives", Wiley-Blackwell, 2003, p. 485

SUMMARY OF THE INVENTION

Problems to be Solved by the Invention

The present invention has been achieved in view of the circumstances described above, and provides: a seed koji for brewing that either does not includes any food items containing allergenic substances as the main raw material and auxiliary raw material or includes only up to an amount that does not induce an allergy in order to prevent carryover of allergenic substances derived not only from the main raw material but also auxiliary raw materials and by which it is possible to produce a soy sauce-like seasoning having a similar flavor to that of soy sauce; and koji for brewing that uses the seed koji for brewing; as well as a soy sauce-like seasoning that uses the koji for brewing.

More specifically, the present invention provides: a seed koji for brewing that either does not includes any allergen for which labeling is either mandatory or recommended on the basis of the Food Sanitation Act as well as any food item specified as an item to be labeled according to CODEX specified by the Joint FAO/WHO Food Standards Programme (Codex Alimentarius Commission) as the main raw material and auxiliary raw material, or includes only up to an amount that does not induce an allergy, in order to prevent carryover of allergenic substances derived not only from the main raw material but also auxiliary raw materials, and by which it is possible to produce a soy sauce-like seasoning having a similar flavor to that of soy sauce; and koji for brewing that uses the seed koji for brewing; as well as a soy sauce-like seasoning that uses the koji for brewing.

Solution to Problem

In order to resolve the above problem, the present inventors diligently examined seed koji producing raw materials to be used in place of wheat bran, and unexpectedly acquired the knowledge by which it is possible to produce allergen-free seed koji by producing seed koji from peas as the raw material. Therefore, it was discovered that the koji for brewing that was obtained by using the allergen-free seed koji, and the soy sauce-like seasoning obtained by using the koji for brewing resolves the problem of carryover of allergenic substances derived from the main raw material and auxiliary raw materials, and also discovered that the soy sauce-like seasoning thus obtained has almost the same or better flavor as regular soy sauce (Koikuchi-type), and the present invention was thus realized.

That is, the present invention relates to a seed koji for brewing that is obtained by inoculating a koji mold belonging to the *Aspergillus* genus into a seed koji raw material, where the seed koji raw material is a pea, koji for brewing that is obtained by using the seed koji for brewing, as well as a soy sauce-like seasoning that is obtained by using the koji for brewing.

Advantageous Effect of the Invention

According to the seed koji for brewing, koji for brewing, and soy sauce-like seasoning of the present invention, it is possible to provide a substitute seasoning of soy sauce that not only patients allergic to soybean and wheat, but also consumers concerned about allergies caused by any of the 27 food items specified within Japan, and eight kinds of food items specified in CODEX are possible to safely use for purposes such as seasoning during cooking and for direct sprinkling on food items.

DESCRIPTION OF THE EMBODIMENT

1. Seed Koji for Brewing and Method of Producing the Same

The seed koji for brewing according to the present embodiment is a seed koji for brewing that is obtained by inoculating koji mold belonging to the *Aspergillus* genus into a seed koji raw material, where the seed koji raw material is peas.

The peas used in the present embodiment may be any type of peas classified into the pea family, including green peas, yellow peas, red peas, podded peas, and snap peas, for example. In order to obtain a liquid seasoning having a quality that is close to that of soy sauce, it is preferable to use green peas and yellow peas, etc. of *Pisum sativum* ssp. *arvense* (L.) Poir.

Before producing seed koji for brewing, the raw material must be processed with the purpose of sterilization and protein denaturation of seed koji raw material. As for the method of processing of the raw material, it is preferable to crack the raw material to an appropriate grain size, thereafter add water, and then perform pressurized steaming and puff-cooking treatment. The processing conditions such as pressure and temperature could conform to those for soybean.

The most important quality index required for seed koji for brewing is the number of spores (also called the number of conidium). If the production of spores is excellent and the number of spores per seed koji weight is large, the growth of the koji mold becomes vigorous during koji-making, and the amount of production of enzymes in koji increases. Therefore, the sugar and amino acid content of the prepared "moromi" increases, and the growth of the lactic acid bacteria and yeast becomes excellent, and at the same time, excellent results are obtained even from the viewpoint of the flavor and aroma of the final product such as soy sauce and fermented soybean paste. Further, if the number of spores of seed koji is large, it is possible to reduce the weight of seed koji added to koji, and thus it is also possible to reduce the production cost.

The peas used in seed koji for brewing according to the present invention are preferably cracked. As for the method of cracking, industrially available cracking machines, such as crushers like roll crushers and milling machines like hammer mill and roll mill, etc. may be used.

From the viewpoint of obtaining a larger number of spores, the grain size of the cracked peas is preferably in the range of 100 to 6000 μm, and more preferably in the range of 500 to 4000 μm. If the grain size is too large, the surface area reduces, because of which the number of spores per weight of peas, which are the seed koji raw material, also reduces and is therefore not preferable. On the other hand, if the grain size is too small, the grains come in close contact with each other, the growth of mycelia on koji mold becomes difficult, and the number of spores becomes less, and is therefore not preferable. It is noted that the grain size may be directly measured and checked by using a ruler or micrometer, and in addition to that, the grains may be sorted by size, by using a sieve having appropriate openings, into the grains that pass through the sieve and those that do not. As for the sieve opening, the mesh number and opening (μm) are defined according to the Japanese Industrial Standards, for example, 500 μm corresponds to #32 mesh and 4000 μm corresponds to #5 mesh.

It is preferable to further include the seed coat of peas as the seed koji raw material. While it depends on the type of seed, the seed coat of peas indicates a thin skin that is approximately 0.1 mm in thickness and covers the cotyledon, radicle, and plumule. By using the seed coat of peas together with the peas as the seed koji raw material, it is possible to secure an appropriate space between the grains of the raw material and to form an appropriate environment for the growth of koji mold from the viewpoint of nutritional balance too, and thus the effect of an increase in the number of spores of koji mold is achieved. It is noted that the seed coat of peas may be obtained by segregating the seed coat that is produced when peas are cracked, with the help of a sieve, etc., or the commercially available seed coat may be used. The commercially available seed coats include, for example, Exafine 2000 (manufactured by Cosucra), etc.

From the viewpoint of obtaining a larger number of spores, the amount of addition of the seed coat of peas is preferably 12.5 to 75.0 wt. %, more preferably 12.5 to 67.5 wt. %, and yet more preferably 12.5 to 32.5 wt. %.

The method of producing seed koji for brewing according to the present invention is as described below. As a culture medium of seed koji, water in an amount of 30 to 120 wt. % based on the weight of the seed koji raw material is mixed with the above-described seed koji raw material (peas and/or seed coat of peas), which is then passed through the steam sterilization process in an autoclave or a well-known seed koji producing machine, etc., and is then cooled to yield a culture medium of seed koji for producing seed koji that does not contain therein any component derived from wheat. If the mixed amount of water is too less, the protein denaturation becomes insufficient, and the growth of koji mold becomes poor. On the other hand, if the mixed amount of water is too much, seed koji solidifies in the form of paste, and the dispersibility during use as seed koji is lost, and is therefore not preferable. The appropriate water content of seed koji after the sterilization process and cooling is approximately 30 to 50 wt. %. Further, as for the sterilization condition, it is possible to use the general sterilization conditions for seed koji for brewing, such as 5 to 30 minutes at 115 to 130° C., as long as the raw material protein is denatured to the appropriate extent, and the saprophytic bacteria in the raw material are killed.

The koji mold used in the present embodiment includes *Aspergillus oryzae*, *Aspergillus sojae*, *Aspergillus niger*, *Aspergillus tamarii*, *Aspergillus kawachii*, *Aspergillus awamori*, *Aspergillus saitoi*, etc.; however, *Aspergillus oryzae* or *Aspergillus sojae* is preferable since they are safe microorganisms that have been used in brewing of soy sauce and fermented soybean paste since the past, and are molds having a high usage frequency in Japanese industries.

In view of growth of the koji mold, sporulation rate, and cost, the amount of addition of source seed koji in seed koji culture medium is preferably 0.01 to 1% of the amount of solid components in the culture medium, and particularly around 0.1%. Further, it is also possible to inoculate an appropriate amount of glycerol stock of koji mold spores and freeze-dried powder.

The seed koji is cultured in the solid seed koji culture medium in a warming condition. The culture temperature is preferably 20 to 40° C., and the culture time could be an optional value, preferably about 72 to 192 hours. Since a temperature of the resulting seed koji will change along with a development of producing processes of the seed koji, the temperature; pH; growth condition, concentration and enzyme activities of the koji mold and other microorganisms are measured and observed with time so that the seed koji may be "homogenized" (In Japanese teire, which means "care"), if necessary, by replacing its surface part with its inner part.

The method of checking the number of spores of seed koji includes sampling an appropriate amount of the seed koji thus obtained, suspending the sampled amount in sterile water containing approximately 0.01% of a surface active agent such as Tween 80, and preparing a spore suspension. When the spore suspension is dropped on a Thoma hemocytometer and the number of spores is counted with the regular method using a microscope, then the number of spores per weight of seed koji is known. In addition, it is also possible to use an automatic grain counting device that is used for a similar purpose.

2. Koji for Brewing and Method for Producing the Same

The koji for brewing according to the present embodiment is obtained by inoculating the above-described seed koji for brewing into peas and performing cultivation.

Although normally, before producing soy sauce koji (koji-making), the raw material is processed with the purpose of denaturing the protein of soybean, it is also possible to process the raw material for the peas used in the present embodiment by a method similar to that for soybean. The widely used industrial methods include performing pressurized steaming and puff-cooking treatment after cracking the raw material to an appropriate grain size. The processing conditions such as pressure and temperature could conform to those for soybean.

In the koji-making process of koji for brewing according to the present embodiment, except the fact that the seed koji for brewing according to the present embodiment is used for the koji mold, it is possible to perform the process in a similar way to that for regular soy sauce koji, and it is also possible to employ methods such as koji-making by using a typical cultivation box (koji-buta) and a method that makes use of a ventilating koji-making device that is widely used industrially. It is possible to obtain koji by adjusting the water content and temperature of the peas for which the raw material has been processed, inoculating the spores (conidia) of the seed koji for brewing according to the present embodiment, and then culturing for 12 to 240 hours at 25 to 45° C. at a humidity level of 85 to 95%. Homogenization (teire) is performed during the process of koji-making in order to regulate the temperature. Further, it is also possible to produce koji by adding whole grains such as rice, which do not contain allergens, and then mixing with powders.

The seed koji for brewing that is obtained based on the present embodiment may also be used as seed koji, etc. for producing enzymes for reagents and medical drugs, in addition to seed koji for brewing for the production of soy sauce, fermented soybean paste, refined sake, etc.

3. Soy Sauce-Like Seasoning and Method of Producing the Same

The soy sauce-like seasoning according to the present embodiment is obtained by preparing the above-described koji for brewing with a salt solution, and then performing fermentation and maturation by lactic acid bacteria and yeasts.

The "soy sauce-like seasoning" according to the present embodiment is a liquid seasoning used for a similar purpose to that of the soy sauce (shoyu) stipulated by the Japanese Agricultural Standards. However, on the basis of the purpose of the present invention, the soy sauce-like seasoning refers to an item that either does not include any food item containing an allergenic substance (allergen) specified as allergens for which labeling is either mandatory or recommended on the basis of the Food Sanitation Act as well as any food item specified as an item to be labeled according to the CODEX specified by the Joint FAO/WHO Food Standards Programme (Codex Alimentarius Commission), or includes only up to an amount that does not induce an allergy, in the main raw material and auxiliary raw material. The soy sauce-like seasoning according to the present embodiment may include auxiliary raw materials such as fruit juice, vegetable soup, various extracts, stocks, saccharides, seasonings, alcoholic beverages, fermented seasonings, acidifiers, and flavoring agents, as long as there is no deviation from the purpose of the present invention.

Here, "food items containing allergenic substances (allergens)" indicates 27 food items specified in Japan as of March 2014 (eggs, milk, wheat, buckwheat, peanuts, abalone, squid, salmon roe, shrimp/prawns, oranges, crab, kiwifruit, beef, walnuts, salmon, mackerel, soybeans, chicken, pork, "matsutake" mushrooms, peaches, bananas, yams, apples, gelatin, sesame, and cashew nuts), and eight kinds of food items specified by CODEX (cereals containing gluten, i.e., wheat, rye, barley, oats, spelt or their hybridized strains and products of these; crustacea and products of these; eggs and egg products; fish and fish products; peanuts, soybeans and products of these; milk and milk products (lactose included); tree nuts and nut products; and food products made of sulfite, or containing 10 mg/kg or more sulfite.)

The method of producing the soy sauce-like seasoning according to the present embodiment is as described below. The above-described koji for brewing is prepared together with a salt solution having an appropriate concentration in the regular preparation proportion in soy sauce brewing, and "moromi" is obtained. While the concentration of salt in the "moromi" juice may differ depending on the preparation temperature, it is preferably around 0.5 to 19%, as long as it is possible to sufficiently inhibit the growth of harmful microorganisms during fermentation. If necessary, *Tetragenococcus halophilus* and *Zygosaccharomyces rouxii* or *Candida versatilis* are added to "moromi", and lactic-acid fermentation and yeast fermentation are performed. Fermentation and maturation is performed for 3 to 6 months while appropriately stirring at 15 to 35° C. according to the regular soy sauce brewing method, or for 1 day to 2 months while appropriately stirring at 35 to 55° C. according to a well-known low-salt high-temperature decomposition method, and matured "moromi" having the flavor of soy sauce is obtained.

While an excellent liquid seasoning having the aroma and umami of soy sauce is obtained even from "moromi" that is obtained from the above-described preparations, when a crudely refined protein obtained by performing extraction, crude refining, and concentration of the protein component from a raw material that does not contain allergens is added during preparation, the soluble total nitrogen (TN), free amino acid, and peptides of the liquid seasoning obtained after fermentation and maturation increases, resulting in an excellent liquid seasoning comparable to high-quality soy sauce. There are no particular restrictions with regard to the crudely refined protein derived from a raw material that does not contain allergens, and for example, a crudely refined protein derived from peas, potato, corn, and rice, etc. may be used. Among these, protein derived from peas is preferable. As the protein derived from peas, for example, Emvital E7 (product name, manufactured by Emsland), PP-CS (product name, manufactured by Organo Food Tech Corporation), Nutralys F85F (product name, manufactured by Roquette), etc. are generally available. From the viewpoint of flavor and protein decomposition ratio, the amount of addition of protein derived from peas is preferably 5 to 100 wt. % of the above-described koji for brewing.

As a method of obtaining a clear soy sauce-like fermented liquid by removing the solid content from matured "moromi", it is possible to use a well-known method such as the filter press method by which "moromi" is wrapped in a filter cloth made of synthetic fibers of nylon, etc. and then folded up and pressurized, or the filter press method by which "moromi" is placed inside a filter cloth pasted on a filtration plate and a compression plate, and then pressurized by compressed air, etc.

Clarification may also be performed for the soy sauce-like seasoning thus obtained. There are no restrictions regarding the clarification method, and a method that is conventionally known may be used, such as the membrane treatment, diatomaceous earth filtration, centrifugal separation, coagulation method, and sedimentation method.

When adding a taste component to the liquid seasoning of the present embodiment in order to adjust the flavor of the soy sauce-like seasoning, there are no particular restrictions regarding food items as long as it does not contain an allergen, and amino acid, yeast extract, nucleic acid, organic acid, protein hydrolysate, saccharides, beet sugar, vegetable extracts, meat extracts, fish sauce, alcoholic beverages, mirin, alcohol, thickeners, emulsifiers, inorganic salts, etc. may be added. It is possible to add these taste components either alone or in combination.

Sterilization or bacteria elimination may also be performed for the soy sauce-like seasoning thus obtained. In the case of sterilization, the soy sauce-like seasoning goes through a heat sterilization process called pasteurization. During pasteurization, the heating conditions performed in the well-known soy sauce making process may be used. It is preferable to perform heating for 20 to 60 minutes at 80 to 85° C., or for 5 to 20 seconds at 110 to 120° C., and then perform cooling thereafter. Since sediment may be produced due to heating, the soy sauce-like seasoning is obtained after allowing to stand still for a few days, and then separating the supernatant from the sediment. Further, in the case of bacteria elimination, filtration and bacteria elimination, etc. are performed through a well-known MF membrane filter, and the filtrate is obtained as the soy sauce-like seasoning.

The soy sauce-like seasoning according to the present invention may be used in a similar way to that of the soy sauce (shoyu) stipulated by the Japanese Agricultural Standards, and may be blended with any food and beverage. For example, the soy sauce-like seasoning may be used by adding to food items such as broths, gravies, ponzu sauce, dressings, soups, sauces, and elements of daily dish.

The sugar alcohols included in the soy sauce-like seasoning according to the present invention for adding umami and mellowness include, for example, arabitol, mannitol, erythritol, sorbitol, galactitol, threitol, xylitol, ribitol, iditol, volemitol, perseitol, inositol, quercitol, etc., and particularly, arabitol, mannitol, erythritol, sorbitol, and galactitol are preferable. Moreover, the amount of addition of these sugar alcohols is preferably 0.01 mg/mL or more. More specifically, as for the amount of addition of each sugar alcohol, 2 mg/mL or more of arabitol, 2 mg/mL or more of mannitol, 1 mg/mL or more of erythritol, 0.3 mg/mL or more of sorbitol, and 0.03 mg/mL or more of galactitol are preferable. Each sugar alcohol may be added either individually, or as a combination of 2 or more sugar alcohols.

Hereinafter, the present invention will be further specifically described with reference to Examples. However, the technical scope of the present invention will not be limited in any way by these Examples.

EXAMPLES

1. Preparation of Seed Koji Using Peas Having Different Cracked-Grain Size
(1) Cracking of Peas Green peas (produced in Canada) were cracked using MILTON Special A type mill (manufactured by Maru-roku Milling Machines). The cracked peas were then sorted by grain size by using a stainless sieve (manufactured by Tokyo Screen Co., Ltd).

(2) Preparation of Seed Koji 4 g of seed koji raw material was put into an erlenmeyer flask having a capacity of 150 mL, to which 3.2 mL of tap water was added and mixed thoroughly. The opening was plugged with cotton, and sterilization was performed for 30 minutes at 121° C. in an autoclave. After cooling, 0.1 g of source seed koji of the koji mold was inoculated and stirred uniformly. The inoculated mixture was stationarily cultured for four days at 30° C.

(3) Measurement of the Number of Spores 2 g of the seed koji thus obtained was sampled, water containing 20 mL of 0.01% Tween80 was added, and the mixture was stirred and suspended vigorously. The suspension was taken up in a dropper and dropped on a Thoma hemocytometer, and the number of spores was measured by using a microscope. It is noted that if the number of spores was too large, the suspension was diluted appropriately before performing microscopy. The results are shown in Table 1. Here, "Not cracked, not sieved" indicates round-shaped peas for which these processes are not performed. "Cracked, but not sieved" indicates that the entire quantity of the cracked peas was used without sorting by sieving. "#5 or above" indicates the grains that were sorted by a #5-mesh sieve, and did not pass through (the grains are larger than the sieve openings). "#8 or above, #5 or below" indicates the grains that did not pass through an #8 mesh from among the grains that had passed through a #5 mesh.

TABLE 1

| Cracked-grain size of peas | No. of spores of seed koji ($\times 10^7$ spores/g) |
|---|---|
| Not cracked, not sieve | 3 |
| Cracked, but not sieved | 290 |
| #5 (4.00-mm opening) or above | 110 |
| #8 (2.36-mm opening) or above | 800 |
| #10 (1.70-mm opening) or above | 1000 |
| #16 (1.00-mm opening) or above | 720 |
| #32 (500-μm opening) or above | 340 |
| #32 (500-μm opening) or less | 96 |
| #8 or above, #5 or below | 1100 |
| #10 or above, #8 or below | 1000 |
| #16 or above, #10 or below | 820 |
| #32 or above, #16 or below | 510 |
| Wheat bran (comparison) | 1100 |

As shown in Table 1, an excellent spore formation was observed even when peas were used as the seed koji raw material. Since the number of spores is approximately $1100 \times 10^7$ spores/g when wheat bran, which is the general seed koji raw material, is used, it can be said that the peas are suitable as seed koji raw material. Particularly, the number of spores increases significantly when peas are cracked as compared to the case when peas are not cracked, and moreover, by sorting the grains of an appropriate grain size by a sieve, the number of spores further increases, and an excellent seed koji is obtained in much the same case as that of the existing wheat bran.

2. Examination of the Amount of Addition of Seed Coat of Peas

When preparing the seed koji, the effect of the amount of addition of the seed coat of peas on the number of spores of seed koji was examined according to the procedures described below. That is, the cracked peas (Cracked, but not sieved) obtained from the above 1 and the seed coat of peas (product name Exafine 2000, manufactured by Cosucra)

were mixed in appropriate amounts, and then the mixture was put into an erlenmeyer flask so that the total weight became 4 g. This mixture was used to prepare seed koji by using a similar manner to that of Example 1, and the number of spores was measured.

TABLE 2

| Cracked peas (wt. %) | Seed coat of peas (wt. %) | No. of spores (×10$^7$ spores/g) |
|---|---|---|
| 100 | 0 | 700 |
| 87.5 | 12.5 | 2000 |
| 75.0 | 25.0 | 2100 |
| 67.5 | 32.5 | 2900 |
| 50 | 50 | 1500 |
| 32.5 | 67.5 | 1300 |
| 25.0 | 75.0 | 1000 |
| 12.5 | 87.5 | 690 |
| 0 | 100 | 300 |

As shown in Table 2, when the seed coat of peas was mixed with cracked peas, the number of spores increased depending on the amount of the addition, and the quality of seed koji improved. However, when the amount of addition of the seed coat of peas exceeded the amount of addition of cracked peas, the number of spores gradually reduced, and when only the seed coat of peas was present, the number of spores reduced. From these results, it became clear that it is possible to obtain excellent seed koji by adding an appropriate amount of the seed coat of peas to the cracked peas.

3. Preparation of Fermented Seasoning of Peas (1) Method of Preparation 1.5 kg of peas (yellow peas, produced in Canada) were cracked by using MILTON Special A type mill (manufactured by Maru-roku Milling Machines), 1 L of water was added and mixed, and the mixture was steamed for three minutes at 121° C. in an autoclave. After allowing the mixture to stand and cool down to 40° C. or below, 2 g of seed koji of peas produced by using the cracked peas (Cracked, but not sieved) obtained from the above 1 was mixed, and the koji-making process was carried out for three days in a constant temperature/humidity machine (temperature 30° C. and humidity 95%) on a cultivation box (Prototype example 1). Moreover, a test section was also prepared in which the seed koji of peas produced by using the cracked peas (Cracked, but not sieved) obtained from the above 1 was inoculated after mixing pregelatinized rice flour in an amount of 20 wt. % of the peas (Prototype example 2). During the koji-making process, teire was performed depending on the growth of the koji mold. 2 L of salt solution was added to the koji thus obtained, which was then stirred well to yield "moromi". At this time, the concentration of salt in "moromi" was 17% w/v. Similar preparation management to that of the regular Koikuchi soy sauce was performed for "moromi", which was then matured through lactic-acid fermentation and yeast fermentation. After 6 months from preparation, "moromi" was placed in a nylon filter cloth, and compression was performed by placing a weight. In addition, diatomaceous earth filtration, pasteurization, and supernatant separating were performed according to the usual method of soy sauce producing, and fermented seasoning of peas (Prototype examples 1, 2) was obtained.

(2) General Component Analysis

The general components of soy sauce were analyzed according to the method specified in the Soy Sauce Test Method (Japan Soy Sauce Research Institute Foundation (ed.), issued on Mar. 1, 1985). The aroma components, such as HEMF (sweet, caramel-like aroma) were analyzed quantitatively according to the gas chromatography method (see Journal of Agricultural and Food Chemistry Vol. 39, 934 (1991)). The results are shown in Table 3. It is noted that as a reference, a commercially available regular Koikuchi soy sauce (manufactured by Kikkoman Corporation) using soybean and wheat as the raw material, was analyzed.

TABLE 3

| Sample name | Total nitrogen (TN) (% w/v) | Salt (% w/v) | Glutamic acid (% w/v) | Lactic acid (% w/v) | Ethanol (% w/v) | pH | Color No. | HEMF (ppm w/v) |
|---|---|---|---|---|---|---|---|---|
| Prototype example 1 | 1.40 | 16.3 | 0.9 | 0.9 | 3.2 | 4.7 | 17 | 14 |
| Prototype example 2 | 1.21 | 15.9 | 0.8 | 0.7 | 3.8 | 4.6 | 25 | 13 |
| Regular Koikuchi soy sauce | 1.68 | 15.8 | 1.0 | 0.9 | 2.9 | 4.8 | 9 | 29 |

The fermented seasoning of peas thus obtained had an appearance and flavor like the regular Koikuchi soy sauce, and was a preferable soy sauce-like seasoning even from the viewpoint of taste. From the analysis values of Table 3, it was understood that the components contributing to the taste were included in almost the same proportion as the regular Koikuchi soy sauce. Moreover, it became clear that HEMF, which is known as the characteristic flavor component of the flavor of soy sauce, was also contained in a sufficient amount.

4. Preparation of a Fermented Seasoning of Peas to which Pea Protein is Added (1) Method of Preparation Similar to the Prototype example 1 described above, the preparation of seed koji and koji producing were performed. The pea koji thus obtained and pea protein (manufactured by Emsland) were mixed in the weight ratio of 90:10 (Prototype example 3), 80:20 (Prototype example 4), and 50:50 (Prototype example 5), and similar to the above 3 (1), after carrying out preparation and fermentation and maturation, filter press and pasteurization were performed, and a fermented seasoning of peas (Prototype examples 3 to 5) was obtained.

(2) General Component Analysis

The results of the analysis performed similarly to the above 3 (2) are shown in Table 4.

TABLE 4

| Sample name | (TN) (% w/v) | Salt (% w/v) | Glutamic acid (% w/v) | Lactic acid (% w/v) | Ethanol (% w/v) | pH | Color No. | HEMF (ppm w/v) |
|---|---|---|---|---|---|---|---|---|
| Prototype example 3 | 1.65 | 16.2 | 1.2 | 1.1 | 3.1 | 4.7 | 16 | 16 |
| Prototype example 4 | 1.89 | 16 | 1.3 | 1.1 | 3.8 | 4.6 | 17 | 15 |
| Prototype example 5 | 2.43 | 15.6 | 1.5 | 1.3 | 2.2 | 4.7 | 21 | 12 |

In Prototype example 1 that was prepared only by pea koji, the total nitrogen (TN) was 1.4 which corresponds to the JAS superior grade soy sauce (see Table 3), but from the results of Table 4, in Prototype example 3 to which pea protein was added during preparation, the total nitrogen (TN) became 1.65 which corresponds to the JAS special grade soy sauce. Moreover, glutamic acid that has a large contribution to the umami of the soy sauce-like seasoning also improved from 0.9 to 1.2. In addition, by increasing the amount of addition of pea protein, the TN and glutamic acid improved depending on the increased amount, and a significantly stronger umami could be tasted. On the other hand, in the recent years, when used as a raw material for processing, the demand for soy sauce having a light color has been increasing. When peas are used as the raw material, the color becomes lighter, and it was found that by adding rice (see Table 3) and pea protein (see Table 4), a soy sauce-like seasoning having a further lighter color was obtained. Since pea protein also does not contain specific allergens, the addition of pea protein made it possible to improve the quality of umami, color, etc. while retaining the characteristic of an allergen-free soy sauce-like seasoning.

5. Sensory Evaluation

The sensory evaluation of each test item was performed by a panel of five trained persons having the discrimination ability, and the taste and aroma of the Prototype example 1 and Prototype example 4 described earlier was evaluated by the semantic differential method in terms of the intensity of umami and soy sauce-like characteristics. Prototype examples 1 and 4 were presented blindly as stock solutions without revealing the contents, and a comparison was made by smelling the aroma and then tasting a quantity of 0.2 mL. The rating scale was based on the criteria described below and the average rating among panelists was calculated.

(Rating Scale)
1. Quite weak or almost no umami/soy sauce-like characteristics
2. Somewhat weak umami/soy sauce-like characteristics
3. Some umami/soy sauce-like characteristics is experienced
4. Somewhat strong umami/soy sauce-like characteristics
5. Quit strong umami/soy sauce-like characteristics

TABLE 5

| Sample name | umami | Soy sauce-like characteristics |
|---|---|---|
| Prototype example 1 | 4.6 | 4.8 |
| Prototype example 4 | 4.8 | 4.4 |

From the sensory evaluation results of Table 5, it was found that both the Prototype examples 1 and 4 have a quite strong umami and soy sauce-like characteristics. The fact that the pH, umami of glutamic acid, organic acid generated by fermentation and maturation, and the color components generated by the Maillard reaction are included in an amount close to that of the regular soybean and wheat soy sauce seems to contribute to the soy sauce-like taste. Further, the fact that the characteristic aroma components of soy sauce generated by fermentation, including the HEMF, are included in an amount close to that of the regular soybean and wheat soy sauce seems to contribute to the soy sauce-like aroma. In addition, it was confirmed that the Prototype example 4 to which pea protein was added had an even stronger umami. It is noted that the comment from the panelists was that "the blind tasting of Prototype examples 1 and 4 indicates soy sauce-like characteristics to an extent that is indistinguishable from the regular soy sauce."

6. Extraction of Sugar Alcohol and Derivatization (1) Test Method

2 μL of each test sample was transferred to a micro tube respectively, 1000 μL of a mixed solution of Methanol:Water:Chloroform (5:2:2) and 60 μL of 0.2 mg/mL of ribitol (manufactured by Wako Pure Chemical Industries, Ltd.) as an internal standard substance were added, and then stirred. After the stirring, centrifugal separation was performed for 16,000×g for three minutes at 4° C., and 900 μL of supernatant was collected and then transferred to another micro tube. Thereafter, 400 μL of distilled water was added, stirred, and performed centrifugal separation again in the similar manner. 900 μL of the supernatant was transferred to yet another micro tube, and was concentrated to become 200 μL or less by a centrifugal concentrator. Thereafter, a dry solid was obtained by using a freeze dryer. Next, the dried solid was dissolved in 100 μL of anhydrous pyridine (manufactured by Wako Pure Chemical Industries, Ltd.) containing 20 mg/mL of methoxyamine hydrochloride (manufactured by Sigma-Aldrich), and was maintained under stirring for 90 minutes at 30° C. Then, 50 μL of N-methyl-N-trimethylsilyl-trifluoro-acetamide (manufactured by GL Sciences Inc.) was added, and trimethylsilylation was performed by allowing the solution to react for 30 minutes at 37° C. to obtain a sample for gas chromatography mass spectrometry (GC/MS).

(2) GC/MS Analysis 7890A-5975C (manufactured by Agilent Technologies) was used for the GC/MS analysis, and as a standard, arabitol, mannitol, erythritol, sorbitol, and galactitol (all manufactured by Wako Pure Chemical Industries, Ltd.) were derivatized and measured in a similar manner, and quantitative determination was performed from the resulting calibration curve. The device conditions were as follows.

Column: CP-SIL 8CB-MS
  (30 mm×0.25 mm, manufactured by Agilent Technologies)
Temperature-rising conditions: After retaining for 2 minutes at 80° C., 80 to 320° C., 15° C./minute, and retention for 6 minutes at 320° C.
Carrier gas and flow rate: Helium gas, 1 mL/minute
Injection temperature: 230° C.

TABLE 6

| Substance name | Prototype example 1 (mg/mL) | Prototype example 4 (mg/mL) | Regular Koikuchi soy sauce (mg/mL) |
|---|---|---|---|
| Arabitol | 9.93 | 5.81 | 1.64 |
| Mannitol | 9.28 | 8.53 | 1.34 |
| Erythritol | 6.20 | 3.79 | 0.63 |
| Sorbitol | 0.53 | 0.46 | 0.24 |
| Galactitol | 0.19 | 0.18 | 0.02 |

From the results of Table 6, it was found that the fermented seasoning of peas contains approximately 2 to 10 times more sugar alcohols as compared to the regular Koikuchi soy sauce. Specifically, the fermented seasoning of peas of the preset invention was found to contain, at least, 2 mg/mL or more of the arabitol, 2 mg/mL or more of the mannitol, 1 mg/mL or more of the erythritol, 0.3 mg/mL or more of the sorbitol, and 0.03 mg/mL or more of the galactitol. Since these sugar alcohols are known to exhibit a unique umami and mellowness, these sugar alcohols are believed to provide preferable characteristics to the taste of the fermented seasoning of peas.

It is possible to blend the sugar alcohols that are not derived from peas, which are the fermented ingredients, as food additives; however, when taking into consideration the recent demand for natural and additive-free food items, sugar alcohols derived from peas, which are the fermented ingredients, are preferable. The fermented seasoning of peas of the present invention is possible to contain sugar alcohols derived from peas in a significant amount, without the use of food additives, by using seed koji produced from a pea raw material and performing fermentation and maturation with natural food materials (particularly, food items like peas that do not contain allergens) as the raw material.

From the above results, by performing fermentation and maturation through the addition of peas, and if necessary, a crudely refined protein derived from food items that do not contain allergens, a soy sauce-like seasoning having the favorable taste and aroma of soy sauce was obtained without the use of any food item containing an allergenic substance. In addition, a seasoning capable of imparting a distinctive umami and richness due to a significant amount of sugar alcohols as compared to the regular soy sauce, was realized. The soy sauce-like seasoning according to the present invention is possible to be used in conventional Japanese cuisine in a similar manner to the soy sauce, and is also possible to be widely used in Chinese and Western cuisines, and thus it is expected to contribute to an improvement in QOL of the eating habits of patients allergic to food items.

The invention claimed is:

1. Seed koji (*Aspergillus* starter) for brewing obtained by inoculating koji mold(s) belonging to an *Aspergillus* genus into a seed koji raw material, wherein the seed koji raw material is a pea.

2. The seed koji for brewing according to claim 1, wherein the pea is a cracked pea.

3. The seed koji for brewing according to claim 2, wherein a grain size of the cracked pea is in a range of 500 to 4000 μm.

4. The seed koji for brewing according to claim 1, further including a seed coat of pea as the seed koji raw material.

5. The seed koji for brewing according to claim 4, wherein an amount of addition of the seed coat of pea is in a range of 12.5 to 75.0 wt. %.

6. Koji for brewing obtained by inoculating the seed koji for brewing according to claim 1 into peas and performing cultivation.

7. A seasoning obtained by producing the koji for brewing according to claim 6 with a salt solution, and then performing fermentation and maturation by lactic acid bacteria and yeast(s).

8. The seasoning according to claim 7, wherein a crudely refined protein derived from a food item that does not contain an allergen is added during preparation.

9. The seasoning according to claim 7, containing one or a plurality of components selected from a group consisting of arabitol, mannitol, erythritol, sorbitol, and galactitol, wherein
the arabitol is in an amount of 2 mg/mL or more,
the mannitol is in an amount of 2 mg/mL or more,
the erythritol is in an amount of 1 mg/mL or more,
the sorbitol is in an amount of 0.3 mg/mL or more, and
the galactitol is in an amount of 0.03 mg/mL or more.

* * * * *